United States Patent [19]

Plank

[11] Patent Number: 4,815,314

[45] Date of Patent: Mar. 28, 1989

[54] PARTICULATE MASS MEASURING APPARATUS

[75] Inventor: Vernon G. Plank, Mansfield, Mass.

[73] Assignee: The United States of America as represented by the Secretary of the Air Force, Washington, D.C.

[21] Appl. No.: 123,626

[22] Filed: Nov. 6, 1987

[51] Int. Cl.$^4$ .............................................. G01N 31/00
[52] U.S. Cl. ........................................................ 73/28
[58] Field of Search ................................ 73/28, 170 R

[56] References Cited

U.S. PATENT DOCUMENTS

| | | | |
|---|---|---|---|
| 2,468,021 | 4/1949 | Black | 73/28 |
| 3,059,470 | 10/1962 | Baldwin et al. | 73/28 |
| 3,104,542 | 9/1961 | Scoggins | 73/28 |
| 3,216,246 | 11/1965 | Blondeau et al. | 73/170 |
| 3,221,541 | 12/1965 | Osborne | 73/28 |
| 3,252,323 | 5/1966 | Torgeson | 73/28 |
| 3,277,724 | 10/1966 | Lundeberg | 73/432 |
| 3,681,973 | 8/1972 | Ludwig | 73/28 |
| 4,159,635 | 7/1979 | Sehmel | 73/28 |

OTHER PUBLICATIONS

Vernon G. Plank, "The M-Meter", Feb. 3, 1987, pp. 171-173, published about Jan. 1987 by University of Miami.

*Primary Examiner*—John Chapman
*Assistant Examiner*—Robert R. Raevis
*Attorney, Agent, or Firm*—Stanton E. Collier; Donald J. Singer

[57] ABSTRACT

An airflow particulate mass measuring apparatus directs the incoming particulate by means of a wedge ring and a central parabolic needle to strike in a capture annulus of a spinner whose change in angular rotation is related to the mass of the particulate striking the spinner. A plurality of torque blades on the spinner cause the particulate to be accelerated and centrifugally ejected.

4 Claims, 4 Drawing Sheets

PARTICULATE MASS MEASURING APPARATUS

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to atmospheric/cloud physics, and, in particular, relates to hydrometeors therein.

It is a well known fact that the atmosphere of Earth and other planets is not purely composed of just gas, of whatever density, but has therein particulate matter such as raindrops, snow, graupel, hail mist, cloud vapor, cloud ice, dust from dust storms and volcanoes, meteoric dust, atomic debris, etc.

One type of prior apparatus used for this endeavor is an air towed pre-weighed filter placed within a housing having an air scoop. This apparatus is towed through the air for a given distance to collect a given volume of air. After, the filter is again weighed to determine the difference in weight which can thus be attributed to the dust collected. Clearly one could select filters having different mesh sizes or one could examine the collected dust to determine particle size ranges in one filter.

A further limitation is that the weighing must take place after the flight. This apparatus is thus limited to particulate matter which does not evaporate. Another limitation is that the actual filter must be weighed afterwards. The spacial-temporal resolution of such device is extremely large and unsatisfactory. An example of this prior apparatus is disclosed in U.S. Pat. No. 2,468,021 which is incorporated by reference.

Other apparatus used to collect particulate are mounted on or near the ground and are fed by gravity or forced air flow. Such apparatus are disclosed in U.S. Pat. Nos. 3,216,246 and 3,104,542 which are incorporated by reference.

This type of apparatus has several disadvantages. For one, they are stationary and near the ground thus limiting the types of samples collected. For example, radioactive material may stay airborne for long periods of time and thus cover long distances and eventually coming to the ground where there are no collectors. Further, meteorological conditions near the ground collector such as winds may distort the sample.

The above disadvantages have motivated a search for an apparatus that minimizes the above disadvantages as well as having additional features that provide advantages over the prior art.

SUMMARY OF THE INVENTION

The present invention is a particulate mass measuring apparatus that overcomes many disadvantages of the above apparatus.

The present invention includes a housing, a spinner, a heater in the spinner, a wedge ring, a needle, a needle heater, and required electronics.

The housing is mountable to an aircraft and has an electrical connector therethrough on a mounting bracket. The rear portion of the housing has a hole therethrough that allows a positive air pressure to exist inside the housing to prevent the entry of moisture. The forward portion of the housing has a central hole therein for mounting and an adjacent hole therein for an optical switch. An electronics package is mounted within the housing.

A spinner heater is mounted on the forward portion of the housing and is in close proximity to the back of the spinner. A wedge ring assembly is mounted also on the forward portion. The wedge ring assembly comprises a wedge ring, ring supports, and a mounting annulus. The ring supports are attached to the wedge ring and the annulus such that an annulur space exists between the two. A spinner is rotatably mounted on a fixed shaft that is mounted in the forward section of the housing. The rear of the spinner has thereon a spoke-like pattern of light and dark which act as counting marks. The optical switch views these marks and outputs a pulsed signal that corresponds to each counting mark. Each pulse corresponding to a mark represents so many degrees of rotation. The number of marks per unit time interval is the critical factor enabling measurement of the rotation rate of the spinner. A conically shaped needle is fixedly mounted to the housing and is positioned in front of the spinner. The base of the needle covers a circular area of the spinner. A heater is placed inside the needle to prevent icing.

The spinner upper surface has shallow blades within a flat central circular area with a bearing mounted therein. An annulus of torque blades are on the outer portion of the spinner. Each torque blade, as viewed from the front of the apparatus, is triangularly shaped having the apex on the inner edge of the annulus. The sides of the triangle are closely tangent to the inner edge. The outer edge of the blade is raised and is directly under the wedge ring. Incoming particulate striking the needle are focused onto the exposed part of the spinner. The needle has a parabolic figure to insure such focusing. Incoming particulate striking the wedge ring are also forced onto the exposed part of the spinner. Since the spinner is rotating at thousands of revolutions per minute, the particulate striking the torque blades in the annulus ring of capture of the spinner cause the spinner to slow; the particulate is eventually ejected from the spinner by aerodynamic and centrifugal forces through channel ports in the outer area of the spinner. Given the change in the spin rate with other parameters and variables, the mass of the particulate is determinable. By appropriate means, this apparatus is able to measure integrated mass flow or individual particulate masses as a mass spectrometer.

Therefore, it is one object of the present invention to provide a particulate mass measuring apparatus for use in air streams.

It is another object of the present invention to provide a particulate mass measuring apparatus having the ability to measure the mass of both total mass captured and individual mass of particulate;

It is another object of the present invention to provide a particulate mass measuring apparatus having heating means therein to prevent icing of various parts;

It is another object of the present invention to provide a particulate mass measuring apparatus having the ability to measure the mass of both liquid and solid particulate matter in the airstream.

It is another object of the present invention to provide a particulate mass measuring apparatus having a computer solved equation to provide measurement information about particulate mass.

These any many other objects and advantages of the present invention will be readily apparent to one skilled in the pertinent art from the following detailed description of a preferred embodiment of the invention and the related drawings.

DETAILED DESCRIPTION OF THE PREFERRED EMBODIMENT

Figure 1:
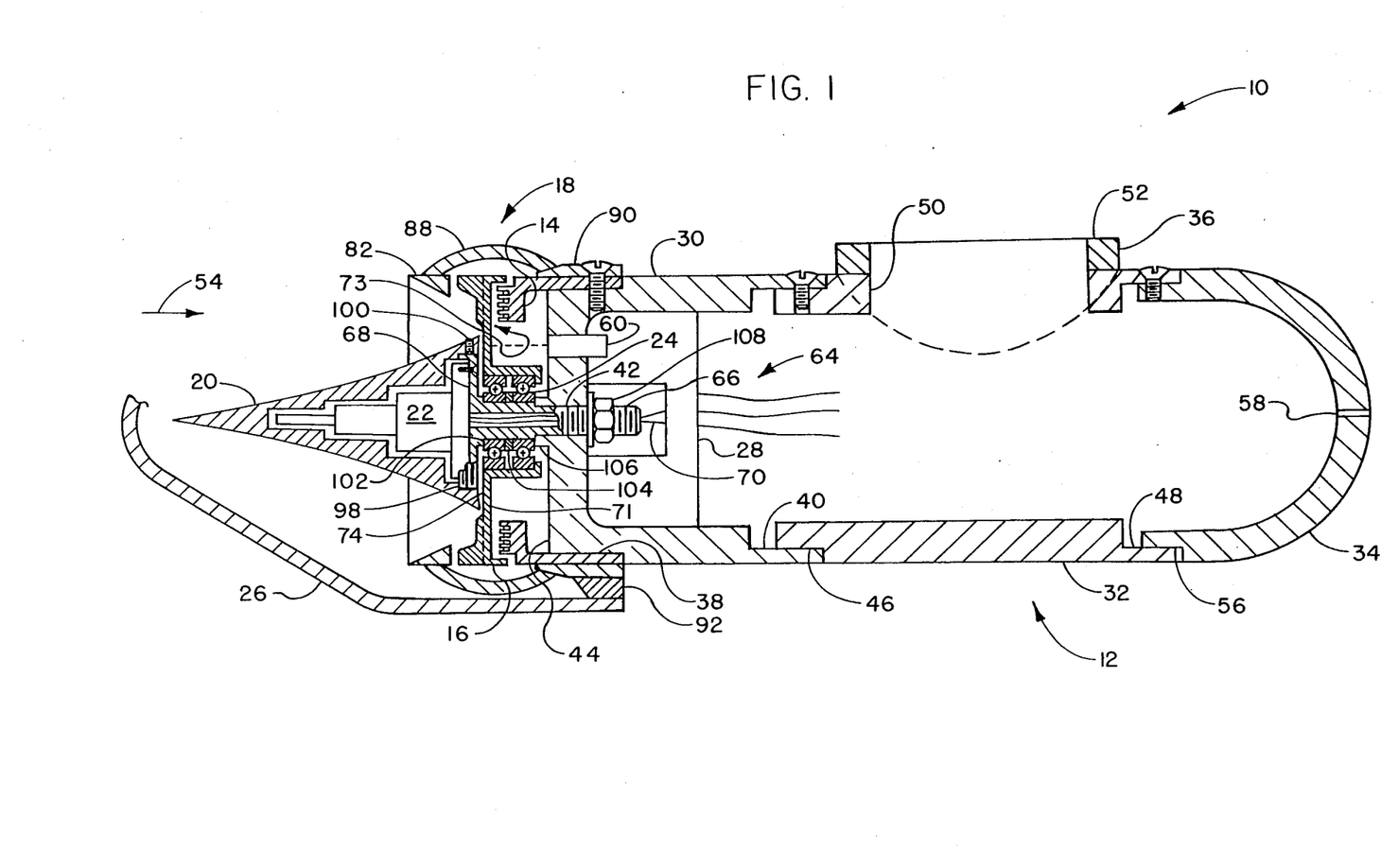
FIG. 1 illustrates by cross section the particulate mass measuring apparatus of the present invention.

Referring to FIG. 1, a particulate mass measuring apparatus 10 is shown in cross section. Apparatus 10 includes a housing 12, a spinner heater section 14, a spinner 16, a wedge ring assembly 18, a needle 20, a needle heater 22, a bearing means 24, a cover 26, and an electronic section 28.

Housing 12 has a forward section 30, a middle section 32, a rear section 34 and a mounting bracket 36. Forward section 30 is a cylindrically shaped cup having ring shaped grooves 38 and 40 on the ends and a shaft hole 42 centered on the front cover 44. Middle section 32 is a cylindrically shaped tube having ring shaped grooves 46 and 48 on the ends and an access port 50 thereon. Mounting bracket 36 is attached thereon by bolting and is attached to an aircraft, not shown, at surface 52 by bolting. Clearly this apparatus 10 can be attached to any vehicle that moves through an air stream. This vehicle obviously should not interfere with the air flow 54 entering apparatus 10. Rear section 34 is aerodynamically shaped and has a ring shaped groove 56 on the front end thereabout for mounting to middle section 32. A cylindrical air hole 58 is placed in the rear end of rear section 34 so that a positive pressure is created inside housing 12 to prevent moisture from entering.

Electronic section 28 is mounted within housing 12. In this embodiment, referring to FIG. 4, optical switch 60 and an operational amplifier 62 are included in this package and the other electronics shown are mounted within the aircraft. Necessary electrical wires 64 are routed through access port 50. The electronics necessary within apparatus 10 are those devices necessary to determine the number of intervals of degree of angular rotation per unit of time.

A fixed, non-rotating shaft 66, being hollow, is bolted to forward section 30. Bearing means 24 allow spinner 16 to rotate freely about shaft 66. Shaft 66 has a mounting flange 68 on its front and on to which needle 20 is mounted by threads 98 and set screws 100. Deicing heater 22 is mounted within needle 20 with electrical wires 70 passing through shaft 66.

The inner races 102 of bearing means 24 having a thrust washer 104 therebetween are held closely between mounting flange 68 and a bearing seat 106 when nut 108 is locked upon shaft 66. Other methods of holding bearing means 24 are clearly possible.

Figure 5:
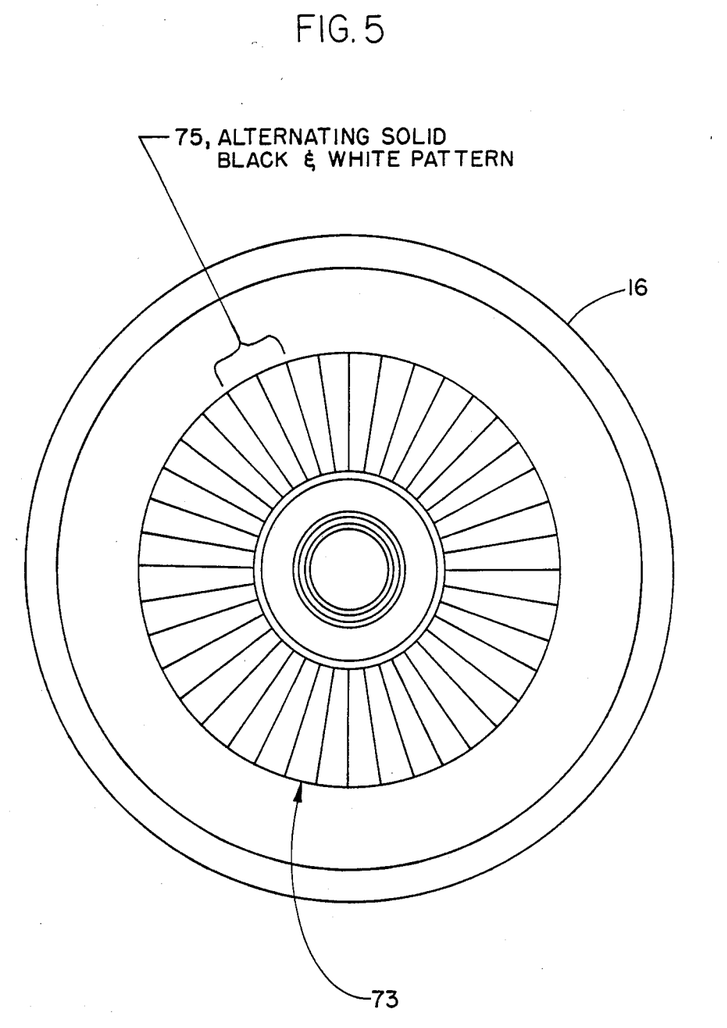
FIG. 5 illustrates by view the back of the spinner.

Referring to FIG. 5, the back 71 of spinner 16 is shown with one version of a counting pattern 73 thereon having counting marks 75. The number of marks 75 is clearly adjustable by changing pattern 73. For example, if one desired to measure total mass, the number of marks need not be as great as when apparatus 10 is used in the mass spectrometer mode. And further, the time interval for counting the passing marks 75 as seen by optical switch 60 must be greater in the total mass mode. Spinner 16 may rotate at 10,000 to 50,000 revolutions per minute depending on mode and air speed.

As an example for purposes of illustration only, assume that the spinner 16 is turning at 12,000 rpm with an error of $0.1\Delta$ caused by changing bearing conditions, etc., in clean air. This equates to $200\pm0.2$ rps or at 20 marks per revolution as $4000\pm4$ mps. If one flew through a cloud, the total count could change by 500 which would equal so much mass in one second, but if one flew in almost clean air examining dust specks, the count may change by only 2 per second but since this falls within the possible error limit the time window must be decreased to a millisecond and thus there should be about $4\pm0.004$ marks per millisecond. Thus a hit by one dust speck would be detected and this apparatus 10 operates as a mass spectrometer. An alternative method is to increase the mark count on pattern 73 rather than change the time interval.

Figure 2:
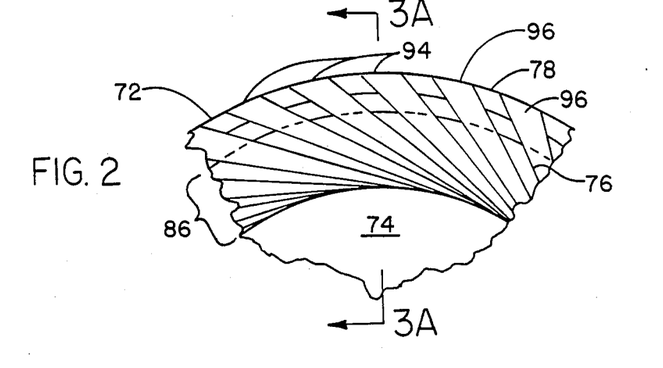
FIG. 2 illustrates by partial view the spinner of the present invention.

FIG. 2 illustrates spinner 16 with the torque blades 72 thereon. A flat area 74 is protected by needle 20 from above. Each blade 72 has a lower blade 76 and an upper blade 78, see also FIG. 3A.

Figure 3A:
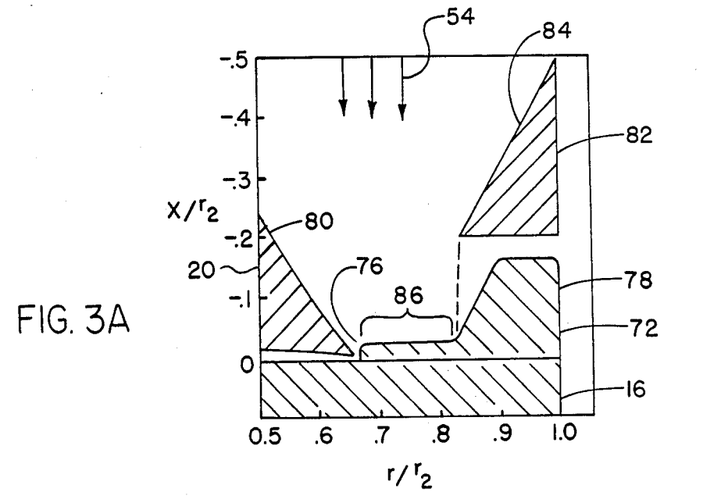
FIGS. 3A and 3B illustrate the spinner cross section and dynamic flow at equilibrium.
Figure 3B:
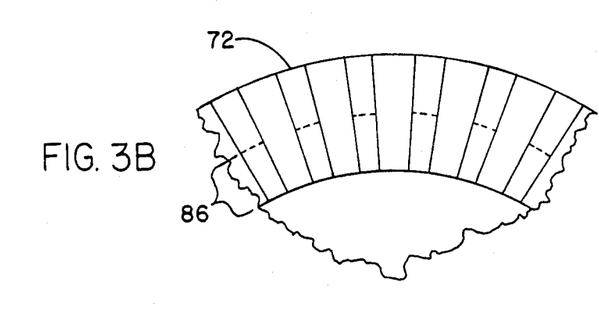

Referring to FIG. 3A, this illustrates a cross section of the spinner 16, needle 20 having a parabolic surface 80 and, a wedge ring 82. As seen thereon, upper blade 78 falls within the "shadow" of wedge ring 82 so that no particulate directly impinges on the upper blade 78. The particulate which strikes wedge ring surface 84 deflects onto the lower blade 76 that forms a capture annulus 86. Further, since surface 80 of needle 20 is parabolic with a focus on the lower blade 76, all incoming particulate striking surface 80 also is focused onto the capture annulus 86. FIG. 3B shows the torque blade 72 approximately as seen by the radial air flow when the spinner 16 is rotating at equilibrium speed.

Returning to FIG. 1, wedge ring assembly 18 includes a circular wedge ring 82, wedge ring supports 88, and a mounting annulus 90 that attaches to spinner heater 14. A cover 26 is attached to an annular mounting ring 92. Cover 26 is removed when operating apparatus 10.

Spinner heater 14 has a flat ring shaped top with a hole therethrough. The ring shaped top has a plurality of concentric grooves therein into which heater wires are positioned. The ring shaped top has a channel about an outer edge for closely accepting a lower lip of spinner 16.

As seen in FIG. 3A, the space between wedge ring 82 and upper blade 78 is minimized so that almost all particulate matter passes through channel ports 94 formed between torque blades, see FIG. 2. This insures that the particulate interacts with the lower torque blades 76 and do not escape thereby.

Figure 4:
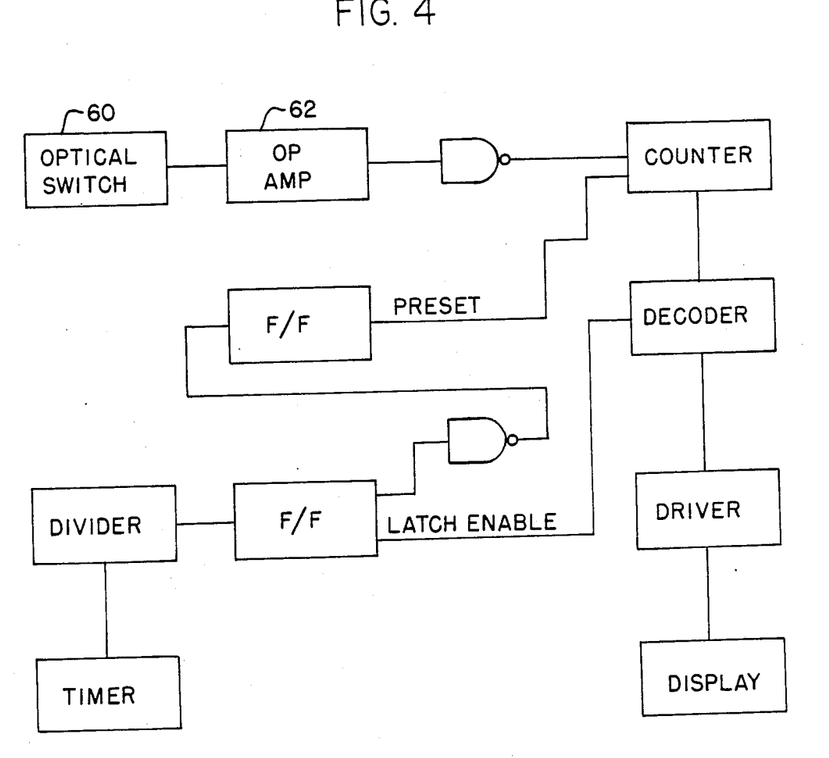
FIG. 4 illustrates by block diagram one embodiment to obtain data from the apparatus of the present invention.

Referring to FIG. 4, an electronic circuit diagram illustrates one embodiment to obtain the number of marks per unit of time. Other circuits or devices are clearly possibly to determine the number of marks per unit of time. A computer, not shown, can record the amount of marks per unit of time. A frequency counter such as a Hewlett-Packard 5384A can be used for counting and display. Additional resolution can be obtained with the use of a shaft encoder rather than the counting pattern 73 of FIG. 5.

In order to determine the particulate mass from apparatus 10, the following equation applies:

$$M = \frac{K_1 F_{bp} Q_\omega}{F_{et} E S} \quad \frac{g}{m^3} \tag{1}$$

In equation (1), S is the true airspeed of the aircraft (or airstream flow), in cm/s; $K_1$ is a particular constant that is described below, in g—cm/(m$^3$—s); E is the aerodynamic collection efficiency of apparatus 10 (for collecting particulates over their total size range, at airstream velocities ; $F_{bp}$ is a factor of bearing performance; $F_{\epsilon t}$ is an energy transfer factor, and $Q_W$ is a rotational quantity that is a variable function of the spinner 16 rotation rate in a clear-air environment, $\omega_a$(-rad/s), as opposed to the rotation rate, ω(rad/s), in a particulate environment (for the same S and air density, ρ, g/cm³, conditions, as the clear environment).

The constant $K_1$, as given by equation (2) is $$K_1 = \frac{U_M I}{A_c r_c^2 t_u} = 1.24086 \times 10^6 \frac{g\ cm}{m^3\ s} \quad (2)$$

where $A_c$ is the aerodynamic-cross-section of apparatus 10 (the sectional area exposed to the airstream flow) (=28.2743 cm²), $r_c$ is the mean collection/capture radius (=2.25 cm), for collecting and capturing particulates within the capture annulus 86, see FIG. 3A, $t_u$ is unit time (=1s, in this example), I is the moment of inertia of spinner 16 (=177.6154 g cm²) and $U_M$ is a units conversion factor (=$10^6$ cm³/m³) needed to transform the specific mass content of the particulates, in cgs units of g/cm³, into conventional units of g/m³.

Two different computational assumptions concerning the aerodynamic collection efficiency, E, were used in wind tunnel tests and in the flight tests.

In the wind tunnel tests, water was either introduced directly into apparatus 10 at locations just in front of the rotating spinner 16, or it was introduced onto the non-rotating, central needle 20 and allowed to "stream-down" the sides 80 of needle 20 to be "caught up by" the spinner blade channels 96. In both cases, care was taken that none of the metered flow of water failed to pass through the instrument, such that the assumption $$E=1.0$$

was always justified.

In the flight tests, resort was made to the aerodynamic modeling work which was performed for various configurations of spinner 16, needle 20 and wedge ring 82. This work utilized potential flow theory, programmed for computer simulation, to compute and illustrate the nature of the streamline flow of air through and around apparatus 10, also the trajectories of particulates that, at an assumed true air speed of 100 m/s, predominantly intersected the face area (to be collected), with relatively few of the trajectories sweeping around the face area (to escape collection).

The ratio of particulates collected to the total number of particulates collected (plus those escaped) is, of course, the collection efficiency, E. It was determined that, for the cited airspeed, and for monodispersed water drops, E had the respective values of 0.941, for drops of 70 μm diameter, 0.856, for drops of 30 μm diameter, and 0.530, for drops of 10 μm diameter. Obviously, for monodispersed drops larger than 70 μm, the E values approach unity rather quickly.

Thus an E value of about 0.90 would be appropriate for most populations of particulates that would be encountered at a true airspeed of $10^4$ cm/s. Thus, using this data point and assuming that E varies with S in the manner $$E=1-e^{-K_2 S} \quad (4)$$

it may be established that $K_2$ has the value, $$K_2=2.3\times10^{-4}\ s/cm \quad (5)$$

Equation 4, with the above K value, provides a reasonable description of the variation of E with S. It yields a zero value of E, for S=0, which must be true, and it yields credible values for other airspeeds. For example, at the sampling speeds of the aircraft used in the flight test program (varying from about 130 to 160 knots, or about 6700 to 8200 cm/s), the equation E values range from 0.78 to 0.85.

The descriptivity of the equation could, of course, be tested by further work of the Norment type, for a variety of airspeeds other than $10^4$ cm/s.

It might be noted that any departures of the true E values from the predicted values will cause relatively minor differences in the M values computed from equation 1. There will be small percentage differences, not important large differences.

The "energy transfer factor" is given by $$F_{\epsilon t} = 1 + \frac{2M\phi^2}{r_c \rho_s} N.D. \quad (6)$$

where M is the modulus of elasticity [or of deformation, or of plastic (permanent) deformation, depending on the specific particulate substance], in g/cm². The quantity $r_c$ is as previously defined, and $\rho_s$ is the density of the particulate substance (which may consist of the broken up pieces of snowflakes/crystals, or, in the case of rain, of small droplets and foam), in g/cm³. The final quantity, φ, specifies the incremental amount, in excess of 1.0, whereby the different angular velocity of the spinner 16, that pertains to the transfer of work (energy), $\omega_W$, exceeds the velocity, ω, that pertains to the transfer of angular kinetic energy of rotation to the particulates, i.e., $$\omega_w = \phi\omega \frac{rad}{s} \quad (7)$$

$F_{\epsilon t}$ is not the total transfer factor; it is merely one component of such a total.

The first term of equation 6 (the quantity "unity") relates to the provision of angular kinetic energy of rotation to the particulate material. The second term of the equation relates to the work provided to the particulates. This may be of two types (1) the mechanical work of the fragmentation, splashing, recombination or deformation of the particulate substance or (2) thermal heat, provided through the mechanical equivalent of energy.

Although equation 6 is presently useful for estimating the order of magnitude of the values of $F_{\epsilon t}$, that might be anticipated with various types of particulates, the values of the quantities M, $\rho_s$, and φ, that enter the work related term, are still under investigation.

In the calibration of apparatus 10, (by flight test comparisons of equation 1 predictions versus Particle Measurement Systems (PMS) measurements of M, for example, or from "water-wind-tunnel" tests); it is the values of $F_{\epsilon t}$ that ar established through the calibration efforts. This is the "calibration factor" of equation 1. Once, through such efforts, the typical values of $F_{\epsilon t}$, have been ascertained for the different classes of particulates, we can, then, with theoretical contributions, begin to understand the typical, normal values of the composite quantity $M\phi^2/\rho_s$, and of the individual entering quantities.

The rotational quantity, $Q_\omega$, of equation 1, is given by the variable ratio $$Q_\omega = \frac{\omega_a^2 - \omega^2}{\omega^2} \tag{8}$$

which specifies the ratio of the squares difference of the clear-air-predicted and apparatus 10 measured rotation rate divided by the square of the measured rate. This quantity must be computed from knowledge of the measured rates, plus independent knowledge of the air density, $\rho$, and the true airspeed of the airstream flow, S. The method of modifying equation 8 to express $\omega_a$ in terms of $\rho$ and S is discussed in the following sub-section.

The clear-air flight tests of apparatus 10 performance at various true air speeds and altitudes (air densities) were conducted. Tests were flown at nominal altitudes of 50 feet (over water, $\rho=0.00126$ g/cm), 7000 feet ($\rho=0.00100$ g/cm$^3$) and 14000 feet ($\rho=0.000770$ g/cm$^3$). True air speeds ranged from 115 knots to 190 knots. Three or four different, particular airspeeds, spanning the range, were flown at each altitude, for representative periods, in which the pilot held the airspeed as constant as possible (within a few tens of cm/s, relative to the real time display of the on-board computer, which the pilot used as a guiding reference). The time resolution of the recorded $\omega$, $\rho$ and S data was 0.1 s.

For each of the test periods, averages were obtained for 100 of the consecutive 0.1 s data points (10 s average) for each of the quantities $\rho$, $\omega_a$ and S, and particularly for the "Bernoulli Factor", $$\omega_a = \frac{\omega_a}{S} \quad \frac{rad}{cm} \tag{9}$$

The previous wind tunnel tests had revealed that $\phi_a$ had a power function dependence on S. The analysis of the clear-air flight test data cited above bore this out and additionally demonstrated that $\phi_a$ also has a power function dependence on $\rho$. The combined show that $\phi_a$ can be described by the equation $$\phi_a = K_3 \rho^q S^p \quad \frac{rad}{cm} \tag{10}$$

where $$K_3 = \frac{\phi_a^*}{\rho^{*q} S^{*p}} \quad \frac{rad \; s^p \; cm^{(3q-p-1)}}{g^q} \tag{11}$$

The constant $K_3$ might be referred to as a "normalization constant." A reference, or normalization, value of air density was defined as, $$\rho^* = 0.001 \; g/cm^3 \tag{12}$$

A reference, or normalization, value of $\phi_a$ (pertaining to the P* and S* conditions) was also defined and symbolized as $\phi_a^*$.

A reference, or normalization, value of the true air speed was defined as $$S^* = 150 \; knots = 7721.865 \; \frac{cm}{s} \tag{13}$$

From the analysis of this flight period of basic reference, it was established that $\phi^*_a$, had the value $$\phi^*_a = 0.28590^{rad/cm} \tag{14}$$

The totality of the other flight period data was then utilized to ascertain that q and p had the values.

$$q = 0.15220 \; N.D, \tag{15}$$

$$p = 0.18039 \; N.D, \tag{16}$$

and that, from equations 12 through 16 substituted into equation 11, $K_3$ had the value $$K_3 = 0.16275 \tag{17}$$

Subsequent substitution of this constant into equation 10, together with the values of q and p, from equations 15 and 16, yields $$\phi_a = 0.16275 \; \rho^{0.1522} S^{0.18039} \tag{18}$$

This is the empirical, general equation for the Bernoulli Factor, as determined from the clear-air flight tests.

The clear-air rotation rate of the apparatus 10, as given by equation 9, solved for $\omega_a$, is $$\omega_a = \phi_a s \tag{19}$$

or, from equation 10, $$\omega_a = K_3 \rho^q S^{1+p} \tag{20}$$

This is the equation that is used to predict the values of $\omega_a$, "that should exist" under the same P and S conditions, as those for flights through particulate environments.

Numerically, from equation 15, 16 and 17, equation 20 becomes $$\omega_a = 0.16275 \; \rho^{0.15220} S^{1.18039} \tag{21}$$

When equation 20 is incorporated into the rotational quantity, $Q_\omega$, of equation 8, $$Q_\omega = \frac{K_3^2 \rho^{2q} S^{2(1+p)} - \omega^2}{\omega^2} \tag{22}$$

This equation could be simplified for computation by doing things like specifying that $$K_4 = K_3{}^2, q' = 2q \text{ and } p' = 2(1+p). \tag{23}$$

However, the secondary specifications are better left to the particular individual, or individuals, who program the equation for computer solution.

It might be noted, with regard to equation 22, also equations 15 and 16, that the value of the exponent on P is $$2q = 0.3044 \tag{24}$$

which is close to the value ⅓. Likewise, the value of the exponent on S is $$2(1+p) = 2.3607 \text{ N.D.} \tag{25}$$

which is close to the value 2. This suggests that these values of ⅓ and 2 may be the values that apply to the theoretical case (of potential flow theory) of a spinner devoid of any of the aerodynamic effects of skin friction and its resultant surface layers of turbulence. The departures of the equation 23 and 24 values from ⅓ and 2 would then be reflective of the real aerodynamic flow relative to that of potential flow.

For computation, when equations 4 and 22 are introduced into equation 1, $$M = \frac{K_1 F_{pb} (K_3{}^2 \rho^{2qS2(1+p)} - \omega^2)}{F_{\epsilon t}(1 - e^{-K2S})S \, \omega^2} \; \frac{g}{m^3} \tag{26}$$

where $K_1$ is given by equation 2 and $F_{bp}$ is obtained as described hereinafter. Thus, except for the "calibration factor", $F_{\epsilon t}$, we have an equation that is a function of the measured rotation rate of the spinner, $\omega$, and of the independently-measured values of $\rho$ and S, as determined from other aircraft instruments. Finally, we come to $F_{\epsilon t}$. We must initially estimate the value of this factor, based on prior experience, or by other means. Such estimate enables us to solve equation 25 for what we might refer to as the "nominal values of M".

In calibration, these nominal values of M may be cross-correlated with other M values acquired independently (such as the M values determined from PMS instruments, or the M values established for a "water-wind-tunnel") and the actual value of $F_{\epsilon t}$ pertaining to the situation of best correlation may be established. This value becomes added to our "stock of experience", concerning the typical $F_{\epsilon t}$ value for the given particulate type.

With regard to plotting, if M is the quantity plotted along the ordinate scale (the unknown, dependent quantity), then Q is the quantity that must be plotted along the abscissa scale (the measured, independent quantity). No other rotational quantity, such as $\omega$, can be universally scaled along the abscissa; they all evidence scale variations dependent on the particular values of $\omega_a$ and $\omega$.

At any rate, for plotting, the M equation $$M = \frac{K_1 F_{bp} Q_\omega}{F_{\epsilon t}(1 - e^{-K2S})S} \; \frac{g}{m^3} \tag{27}$$

is required.

The primary point, here, is that, if M is going to be computed from equation 25, then as part of the computational program, $Q\omega$ should be computed from equation 22 in a separate sub-routine and stored, for later use in plotting.

Clearly, many modifications and variations of the present invention are possible in light of the above teachings and it is therefore understood, that within the inventive scope of the inventive concept, the invention may be practiced otherwise than specifically claimed.

What is claimed is:

1. A particulate mass measuring apparatus, said apparatus comprising:

a housing, said housing having a forward section, a middle section, and a rear section; said rear section having an air hole therethrough for placing a positive pressure on a void of said housing, said middle section having an access port therethrough for electrical wires, and said forward section having a shaft holding means and a hole therethrough;

a mounting bracket, said mounting bracket attached to said housing and having a hole therethrough for electrical wires, said hole being aligned with said access port of said housing, said mounting bracket attaching to a vehicle that travels through the air;

a spinner heater, said spinner heater mounted to said forward section of said housing;

a stationary shaft with a mounting flange, said shaft being threaded on one end opposite said mounting flange, said shaft connected to said shaft holding means of said housing, said shaft being hollow therethrough for electrical wires;

a needle, said needle having a parabolic shape thereon such that incoming particulate is focused on to a capture annulus, said needle attached to said mounting flange on said shaft, said needle having a pointed tip and a circular base, said parabolic shape being between said tip and said base;

bearing means, said bearing means attached to said shaft;

an angular momentum means, said angular momentum means attached to said bearing means whereby said angular momentum means rotates about said shaft when in an air flow, said angular momentum means having a plurality of blades thereon for rotating said angular momentum means when in an air flow and for capturing said incoming particulate, said particulate once captured, receiving angular momentum from said angular momentum means before ejection therefrom, whereby the change in angular momentum before and after capture of said particulate is related to the mass of said particulate;

a wedge ring assembly, said assembly comprising:

a wedge ring, said wedge ring having a right triangular shape in cross section, ring supports, said rings supports attached to an outer surface of said wedge ring; and a mounting annulus, said ring supports attached to said mounting annulus, said mounting annulus attached to said housing, a removable means for covering said needle, said wedge ring assembly, said angular momentum means and said spinner heater; and a means for indicating angular rotation of said angular momentum means in an interval of time mounted in said housing.

2. An apparatus as defined in claim 1 wherein said spinner heater has a flat ring shaped top with a hole therethrough, said ring shaped top having a plurality of concentric grooves therein into which heater wires are positioned, said ring shaped top having a channel about an outer edge.

3. An apparatus as defined in claim 2 wherein said angular momentum means is a spinner, said spinner attached to said bearing means such that said spinner rotates about said shaft freely, said spinner comprising:
- a flat circular disk having a hole in the center thereof;
- a bearing holding means, said bearing holding means fixedly attached about said hole in the center of said disk;
- a lip, said lip attached about the outer edge of said disk and being in close proximity to said channel of said spinner heater to prevent the entrance of moisture;
- said plurality of torque blades, said blades attached integrally to the top of said disk, each of said torque blades being shaped like obtuse triangles in a horizontal plane, each tip of said triangles being located at a given radius from the center of said disk, each of said triangles, in a vertical plane, having a lower blade and an upper blade, between each of said triangles is a flow channel, the annulus formed by said lower blades being said capture annulus.

4. An apparatus as defined in claim 3 wherein said upper blades of said spinner are in the shadow of said wedge ring whereby incoming particulate impacting said wedge ring is deflected to said capture annulus.

* * * * *